US009759229B2

(12) United States Patent
Baumgartner et al.

(10) Patent No.: US 9,759,229 B2
(45) Date of Patent: Sep. 12, 2017

(54) BLOOD PUMP INCLUDING A ROTOR

(75) Inventors: Robert Baumgartner, Würselen (DE); Benjamin Mattern, Aachen (DE); Andreas Henseler, Simmerath (DE)

(73) Assignee: MEDOS MEDIZINTECHNIK AG, Stolberg (DE)

( * ) Notice: Subject to any disclaimer, the term of this patent is extended or adjusted under 35 U.S.C. 154(b) by 1094 days.

(21) Appl. No.: 13/695,921

(22) PCT Filed: Apr. 29, 2011

(86) PCT No.: PCT/DE2011/001004
§ 371 (c)(1),
(2), (4) Date: Jan. 22, 2013

(87) PCT Pub. No.: WO2012/006976
PCT Pub. Date: Jan. 19, 2012

(65) Prior Publication Data
US 2013/0115070 A1 May 9, 2013

(30) Foreign Application Priority Data

May 4, 2010 (DE) .................. 10 2010 019 403
Jun. 22, 2010 (DE) .................. 10 2010 024 650

(51) Int. Cl.
*A61M 1/10* (2006.01)
*F04D 29/42* (2006.01)
*F04D 29/58* (2006.01)
*F04D 13/06* (2006.01)

(52) U.S. Cl.
CPC .......... *F04D 29/426* (2013.01); *A61M 1/101* (2013.01); *F04D 13/0633* (2013.01); *F04D 29/588* (2013.01)

(58) Field of Classification Search
CPC .. F04D 13/024; F04D 13/026; F04D 13/0633; F04D 29/0467; F04D 29/426; A61M 1/1013; A61M 1/1025; A61M 1/1036; A61M 1/101; A61M 1/1015
USPC ........................................................ 415/900
See application file for complete search history.

(56) References Cited

U.S. PATENT DOCUMENTS

| 4,135,253 | A | * | 1/1979 | Reich | .................... | A61M 1/101 |
| | | | | | | 415/112 |
| 4,606,698 | A | * | 8/1986 | Clausen | ................ | A61M 1/101 |
| | | | | | | 277/328 |
| 4,643,641 | A | | 2/1987 | Clausen et al. | | |
| 4,984,972 | A | | 1/1991 | Clausen et al. | | |

(Continued)

FOREIGN PATENT DOCUMENTS

DE 10 2006 036948 A1 2/2008
DE WO 2008017289 A2 * 2/2008 ............ A61M 1/101
(Continued)

OTHER PUBLICATIONS

International Search Report issued by the European Patent Office with regard to the corresponding International Patent Application No. PCT/DE2011/001004.

*Primary Examiner* — Justin Seabe
(74) *Attorney, Agent, or Firm* — Henry M. Feiereisen LLC

(57) ABSTRACT

A blood pump includes a rotor mounted in a pump housing via a bearing. The housing includes a metal rod extending from the outer wall of the housing towards the inner side of the housing. The rod allows dissipating heat and has a stabilizing action.

22 Claims, 2 Drawing Sheets

(56) References Cited

U.S. PATENT DOCUMENTS

| | | | | |
|---|---|---|---|---|
| 5,399,145 | A | * | 3/1995 | Ito .......................... A61M 1/101 600/16 |
| 5,575,630 | A | * | 11/1996 | Nakazawa ............ A61M 1/101 415/900 |
| 2004/0091354 | A1 | | 5/2004 | Araki et al. |
| 2006/0024182 | A1 | * | 2/2006 | Akdis ................... F04D 29/047 417/423.12 |
| 2011/0238172 | A1 | | 9/2011 | Akdis et al. |

FOREIGN PATENT DOCUMENTS

| | | |
|---|---|---|
| EP | 2 127 691 A1 | 12/2009 |
| GB | 1 383 811 A | 2/1974 |
| WO | WO 99/53974 A2 | 10/1999 |
| WO | WO 2005/028000 A1 | 3/2005 |
| WO | WO 2007/084339 A2 | 7/2007 |

* cited by examiner

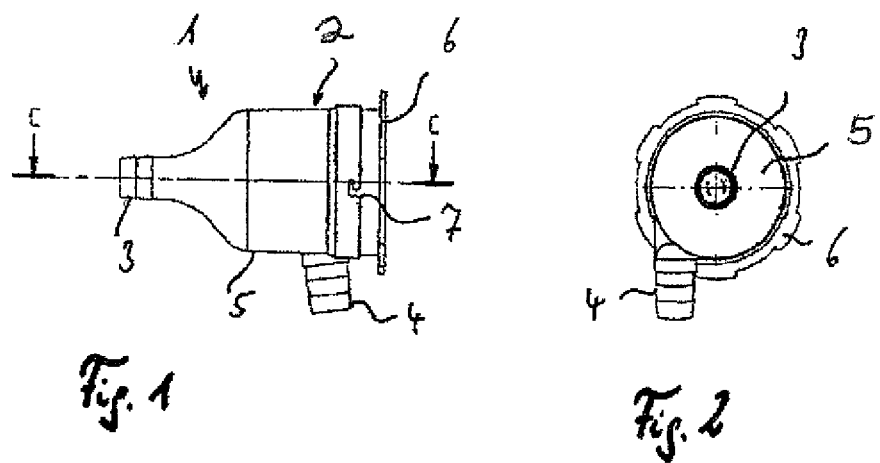
Fig. 1
Fig. 2
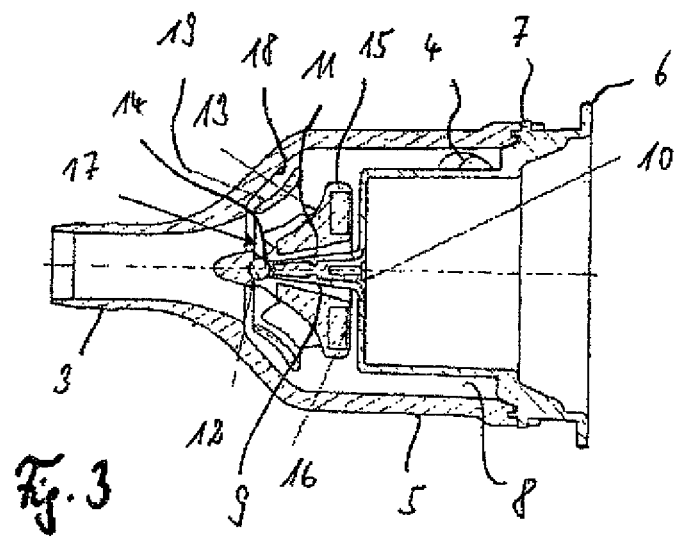
Fig. 3

BLOOD PUMP INCLUDING A ROTOR

CROSS-REFERENCES TO RELATED APPLICATIONS

This application is the U.S. National Stage of International Application No. PCT/DE2011/001004, filed Apr. 29, 2011, which designated the United States and has been published as International Publication No. WO 2012/006976 A2 and which claims the priority of German Patent Application, Serial No. 10 2010 019 403.4, filed May 4, 2010, and German Patent Application, Serial No. 10 2010 024 650.6 filed Jun. 22, 2010, pursuant to 35 U.S.C. 119(a)-(d).

BACKGROUND OF THE INVENTION

The invention n relates to a blood pump including a rotor, which is mounted via a bearing in a pump housing.

Such blood pumps are known in various embodiments. Firstly, a differentiation was made between radial and axial pumps. Particularly good results were achieved with a diagonal flow. The invention therefore relates in particular to the field of diagonal pumps.

An essential area of use of such blood pumps is the conveying of human blood within extracorporeal circuits. The blood pump then takes over completely or partially the pumping function of the heart, and it can be used to assist the heart, for regeneration or bridging for a period of several days. The usage takes place in connection with the clinically conventional components such as PVC tube systems, oxygenators, arterial filters and, if required, various reservoirs. Instead of a PVC tube system, silicone tube pieces up to entire silicone tube systems can also be used.

Special consoles, which can also take over the drive, serve for control, energy supply and monitoring.

It is advantageous in such pumps if the principle of magnetic coupling is used, in order to uncouple the blood component from the drive component. This makes it possible to keep the blood-conducting surfaces very small. A compact construction enables a usage which is patient-friendly and is close to the patient.

In such blood pumps, the rotor is preferably mounted on a ball bearing of ceramic or of aluminium oxide. Forces which can lead to a heating or damage of the pump act in the region of the bearing.

The invention is therefore based on the problem of further developing such a blood pump.

SUMMARY OF THE INVENTION

This problem is solved with a generic blood pump in which the housing has a metal rod extending from the outer wall of the housing towards the inner side of the housing.

Such a rod of a stable and heat-conductive material makes it possible on the one hand to dissipate heat through the housing wall and on the other hand to stabilize housing parts projecting inwards from the housing. The blood pump here does not need either a shaft or dynamic seals.

It is particularly advantageous if the rod is constructed so as to be tapered. It thus permits heat to be received from a special point within the housing and to conduct it away to the outer side of the housing. In addition, a tapered construction of the rod makes an especial mechanical stability possible.

In order to prevent the rod from coming into contact with the blood which is directed in the housing, it is proposed that the rod is arranged in a tapered shaping of the housing. The rod can therefore convey heat out from the interior of the housing and in particular out from the bearing region, without coming into contact with the blood itself. It is particularly advantageous here if the rod is brought close up to the bearing, in order to convey heat out from the bearing region and to stabilize the bearing region.

In order to position the bearing as closely as possible at the blood inlet, it is proposed that the tapered housing shaping extends within the blades and preferably over the entire length of the blades. Thereby, it is achieved that the blades of the rotor are arranged radially outside the tapered rod and radially outside the tapered housing shaping. Therefore, heat occurring between the stationary tapered housing shaping and the rotor is conveyed away by the metal rod.

The rotor can rotate continuously or intermittently. In particular for a quick acceleration of the rotor, it is proposed that the diameter of the rotor is less than 30 mm, preferably less than 28 mm. The small diameter reduces the inertia forces and thereby facilitates the acceleration. Therefore, the rotor can also be ideally used for pulsatile use. In pulsatile operation, a rotation speed of 100 l/min up to 2500 l/min in steps of 100 is proposed. The frequency is then 40 to 90 l/min.

In particular in connection with the small diameter, it is advantageous if the weight of the rotor is kept as small as possible. Thereby, the mass inertia forces are reduced, in order to facilitate the acceleration. In an advantageous variant embodiment, the rotor has a weight of less than 10 g, preferably even less than 8.5 g.

In a corresponding manner, the diameter of the rotor covering disc can be less than 32 mm, preferably less than 30 mm.

The specific construction of the rotor and of the cover disc is also essential to the invention independently of the remaining features of the invention.

A further feature also essential to the invention independently of the remaining features lies in the construction of the housing. In order to separate the drive unit from the "blood component" in a simple manner, it is proposed that the housing has a radially outer housing wall and a motor mount extending into it. The motor can thereby be separated easily from the housing, and the housing is used at the same time as a motor mounting.

A particularly compact construction is achieved in that an annular gap is formed between the radially outer housing wall and the motor mount. Blood which flows from the rotor to the blood outlet can be directed in this annular gap. By the uncoupling of the blood component and the drive component, it becomes possible to use the drive unit several times and to keep the blood-directing surface very small. The pump material is selected here so that it can be coated with a coating inhibiting blood coagulation, such as for example Reoparin or Bioline.

It is advantageous if the rotor has at least one coupling magnet in order to transfer a torque from a motor in a contactless manner to the rotor. For this, segment magnets arranged in the rotor, or a ring magnet can be used. The use of a ring magnet is also essential to the invention independently of the previously mentioned features. In a preferred example embodiment the coupling magnet here has a magnetic yoke. In so far as the front side of the rotor faces the motor, the yoke is arranged on the rear side of the rotor. The yoke connects the segment magnets and makes provision that a magnetic field intensity can occur between the rotor and the drive magnet, by which a force of over 20 N can be transferred.

Furthermore, it is advantageous if the rotor has a flushing bore which leads to the bearing.

A high degree of friction occurs on the bearing, with the consequence of a great development of heat. As previously described, this heat can be conveyed off by a rod with good thermal conductivity, which is preferably made from steel. Alternatively or cumulatively, it is proposed that the rotor is mounted in the pump housing over a bearing with a spherical segment lying in a bearing shell. The spherical segment here should have as a maximum the radius of the bearing shell, in order to lie securely in the bearing. Preferably, the radius of the spherical segment is smaller than the radius of the bearing shell, so that a point bearing is produced. The spherical segment can be a part of a ball here. The construction of the bearing is also essential to the invention independently of the previously mentioned features.

The spherical segment can be constructed here on the rod and on the rotor. It has been found that it is advantageous if the rotor has the spherical segment.

So that as little wear as possible occurs and in order to ensure a good heat dissipation, it is proposed that a portion of the bearing is produced from PTFE, steel, ceramic or glass, preferably borosilicate glass. This part is preferably the spherical segment or the ball, whereas the rod is preferably produced from steel. The choice of the materials is also essential to the invention independently of the previously mentioned features.

As temperatures of over 200° C. can occur in the housing, especially in the region of the bearing, it is proposed that at least a portion of the housing is produced from a polyether ketone. These are thermoplastic plastics resistant to high temperatures, such as for example polyether ether ketone (PEEK). This feature is also essential to the invention independently of the previously mentioned features.

A particular structural construction makes it possible to produce such a blood pump in which the priming volume is below 17 ml, preferably below 15 ml.

BRIEF DESCRIPTION OF THE DRAWING

An example embodiment of a blood pump according to the invention is illustrated in the drawings and is explained in further detail below. There are shown:

FIG. 1 a side view of the blood pump

FIG. 2 a top view onto the blood pump shown in FIG. 1

FIG. 3 a section through the blood pump shown in FIG. 1 along the line C-C

DETAILED DESCRIPTION OF THE PREFERRED EMBODIMENTS

Figure 4:
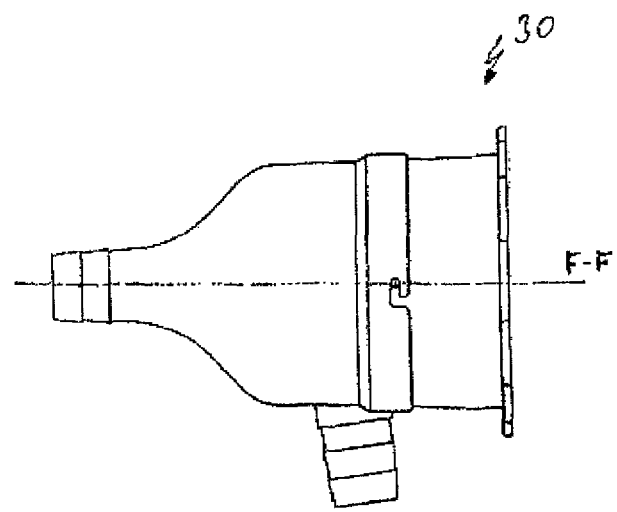
FIG. 4 a side view of an alternative embodiment of the blood pump

The blood pump 1 shown in FIG. 1 has a pump housing 2 with an inlet 3 and an outlet 4.

The pump housing 2 is formed by a radially outer housing wall portion 5 and another housing wall portion which forms a motor mount 6 extending into the radially outer wall portion 5. The motor mount 6 is connected with the outer housing wall 5 in a form-fitting manner via a closure 7.

The motor mount 6 projects into the housing wall portion 5 such that an annular gap 8 is formed between the housing wall portion 5 and the motor mount 6. Coaxially to the inlet 3, on the motor mount 6, a tapered housing shaping 9 is formed, into which a rod 10 extends in a tapered manner. The rod 10 is securely connected with the tapered housing shaping 9 via an indentation 11.

A ball bearing 12, which is adhered securely with a rotor 13, is situated at the tip of the tapered housing shaping 9. This ball bearing 12 runs in a calotte form of the tapered housing shaping 9 with the rod 10 arranged therein. Thereby, the rotor 13 is mounted in the pump housing 2 by means of the bearing 14.

The rotor 13 has blades 15, on which coupling magnets 16 are fastened, in order to transfer the torque of a motor (not shown) in a contactless manner to the rotor 13. The coupling magnets 16 in the rotor 13 can be configured as individual quarter segment magnets. A ring magnet is advantageous.

The rotor 13 has a diameter of approximately 26 mm and in the vicinity of the bearing 14 has a flushing bore 17 via which blood flows from the inlet 3 to the bearing 14.

A rotor cover disc 19, which has a diameter of approx. 28 mm, is arranged between the rotor 13 and the inner side 18 of the housing.

The blood pump can be used for a period of at least seven days. The duration of application extends from up to 6 hours to several weeks. In practice, it has been found hitherto that the pump readily withstands a continuous use of more than 50 days. The diagonal-shaped blade wheel and hence the diagonal-shaped direction of flow combine the advantages of centrifugal pumps and axial pumps. The pump generates in a rotation rate range of 0 to 10 000 r/min a continuous or a pulsatile volume flow of 0 to 8 liters per minute with a maximum pressure difference of up to 650 mmHg. The maximum delivery pressure generally likes somewhat below 600 mmHg.

The pump head, which, is delivered sterile and pyrogen-free, is able to be stored for at least three years and is sufficiently protected from transportation damage.

Figure 5:
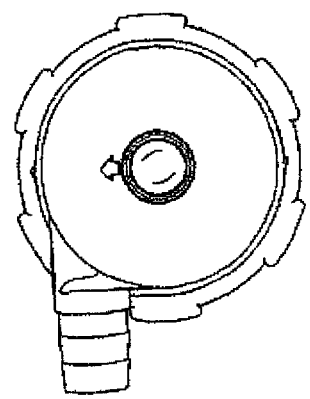
FIG. 5 a top view onto the blood pump shown in FIG. 4.
Figure 6:
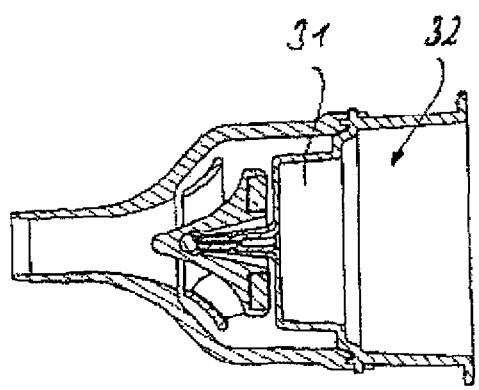
FIG. 6 a section through the blood pump shown in FIG. 4 along the line F-F.

FIGS. 4 to 6 show a slightly modified embodiment of a blood pump 30. Whereas the embodiment shown in FIGS. 1 to 3 has a priming volume of 16 ml, the priming volume in this modified embodiment lies at below 15 ml. This is achieved by a shortened part 31 of the motor mount 32 projecting into the pump.

The invention claimed is:

1. A blood pump, comprising:
    a pump housing, said pump housing comprising a housing wall, said housing wall having a tapered housing shaping defining a tapered recess, said tapered recess projecting into an inside of the housing and opening to an outside of the housing and being fluidly separated from the inside of the housing;
    a tapered metal rod arranged entirely in the tapered recess; and
    a rotor mounted in the inside of the pump housing via a bearing arranged in the inside of the housing.

2. The blood pump of claim 1, wherein the rotor has blades in surrounding relationship with the tapered housing shaping.

3. The blood pump of claim 2, wherein the tapered housing shaping extends over an entire length of the blades.

4. The blood pump of claim 1, wherein a diameter of the rotor is less than 30 mm.

5. The blood pump of claim 4, wherein the diameter of the rotor is less than 28 mm.

6. The blood pump of claim 1, further comprising a rotor cover disc, said rotor cover disc having a diameter of less than 32 mm.

7. The blood pump of claim 6, wherein the rotor cover disc has a diameter of less than 30 mm.

8. The blood pump of claim 1, wherein the rotor has a weight of less than 10 g.

9. The blood pump of claim 8, wherein the rotor has a weight of less than 8.5 g.

10. The blood pump of claim 1, wherein the housing wall comprises a radially outer portion and a portion extending radially inwardly relative to the radially outer portion so as to form a motor mount, wherein the motor mount is form fittingly connected with the radially outer portion via a closure, and wherein an annular gap is formed between the radially outer portion and the motor mount.

11. The blood pump of claim 1, wherein the rotor comprises at least one coupling magnet for contactlessly transferring a torque from a motor to the rotor.

12. The blood pump of claim 1, wherein the rotor has a flushing bore, said flushing bore leading to the bearing.

13. The blood pump of claim 1, wherein the bearing comprises a bearing shell and a spherical segment received in the bearing shell.

14. The blood pump of claim 13, wherein the spherical segment is formed on the rotor.

15. The blood pump of claim 1, wherein a portion of the bearing is made of polytetrafluoroethylene.

16. The blood pump of claim 1, wherein a portion of the bearing is made of high-grade steel.

17. The blood pump of claim 1, wherein a portion of the bearing is made of ceramic or glass.

18. The blood pump of claim 17, wherein the glass is a silicate glass.

19. The blood pump of claim 1, wherein at least a portion of the housing is made of a polyether ketone.

20. The blood pump of claim 1, wherein a priming volume of the blood pump is below 17 ml.

21. The blood pump of claim 20, wherein the priming volume is below 15 ml.

22. The blood pump of claim 1, wherein the rotor is supported on the bearing for rotation relative to the metal rod.

* * * * *